(12) United States Patent
Dalke et al.

(10) Patent No.: US 7,015,451 B2
(45) Date of Patent: Mar. 21, 2006

(54) POWER SUPPLY RAIL CONTROLLER

(75) Inventors: David Dalke, Irvine, CA (US); Robert Smith, Lake Forest, CA (US); Ammar Al-Ali, Tustin, CA (US); Mohamed K. Diab, Mission Viejo, CA (US); Ronald Coverston, Portola Hills, CA (US)

(73) Assignee: Masimo Corporation, Irvine, CA (US)

( * ) Notice: Subject to any disclaimer, the term of this patent is extended or adjusted under 35 U.S.C. 154(b) by 490 days.

(21) Appl. No.: 10/351,961

(22) Filed: Jan. 24, 2003

(65) Prior Publication Data

US 2003/0218386 A1    Nov. 27, 2003

Related U.S. Application Data

(60) Provisional application No. 60/351,751, filed on Jan. 25, 2002.

(51) Int. Cl.
    *H01J 40/14*    (2006.01)
(52) U.S. Cl. ................ 250/214 A; 250/214 R

(58) Field of Classification Search ............ None
    See application file for complete search history.

(56) References Cited

U.S. PATENT DOCUMENTS

| 5,068,540 A | * | 11/1991 | Tsuji ............... 250/559.38 |
| 6,081,735 A | | 6/2000 | Diab et al. |
| 6,088,607 A | | 7/2000 | Diab et al. |

\* cited by examiner

*Primary Examiner*—Que T. Le
(74) *Attorney, Agent, or Firm*—Knobbe, Martens, Olson & Bear, LLP

(57) ABSTRACT

A power supply rail controller operates on an analog component having a signal input, a power input and a signal output. A voltage controller provides a control output responsive to the signal output. A power supply generates a voltage for the power input, where the voltage is responsive to the control output. The voltage is reduced in magnitude to reduce power dissipation and increased in magnitude to avoid signal distortion.

20 Claims, 6 Drawing Sheets

POWER SUPPLY RAIL CONTROLLER

CROSS-REFERENCE TO RELATED APPLICATIONS

The present application claims priority benefit under 35 U.S.C. §119(e) from U.S. Provisional Application No. 60/351,751, filed Jan. 25, 2002, entitled "Differential Input, Power Efficient Pulse Oximeter Preamplifer," which are incorporated herein by reference.

BACKGROUND OF THE INVENTION

A detector preamplifier is an optical receiver component utilized in a variety of applications including pulse oximetry. Pulse oximetry is a noninvasive, easy to use, inexpensive procedure for monitoring blood oxygen that has gained rapid acceptance in a wide variety of medical applications, including surgical wards, intensive care units, general wards and home care. A pulse oximeter sensor detects the light absorption characteristics of blood perfused tissue, and a corresponding monitor performs a blood spectral analysis based upon the sensor signal. By monitoring for decreases in the arterial oxygen supply, pulse oximeters reduce the risk of accidental death and injury.

FIG. 1 illustrates an analog portion of a pulse oximetry system 100 having a sensor 110 and a monitor 150. The sensor 110 has emitters 120 and a detector 130. The emitters 120 typically consist of a red LED (light emitting diode) and an infrared LED that project light through blood vessels and capillaries underneath a tissue site, such as a fingernail bed. The detector 130 is typically a photodiode positioned so as to detect light transmitted through or reflected from the tissue site. The signal current generated by the detector 130 is proportional to the intensity of the light emerging from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

Also shown in FIG. 1, the monitor 150 has drivers 160, a preamplifier 200, signal conditioning 180 and digitization 190. The drivers 160 alternately activate the emitters 120. The preamplifier 200 provides an amplified detector signal for signal conditioning 180, which typically includes filtering and additional amplification. The digitization 190 performs an analog-to-digital conversion (ADC) of the conditioned detector signal. The resulting digitized signal is then analyzed by a digital signal processor (not shown) to determine oxygen saturation based upon the differential absorption by arterial blood of the two wavelengths projected by the emitters 120. A pulse oximetry signal processor is described in U.S. Pat. No. 6,081,735 entitled "Signal Processing Apparatus," which is assigned to Masimo Corporation, Irvine, Calif. and incorporated by reference herein.

FIG. 2 illustrates a circuit for a conventional pulse oximeter preamplifer 200. Other names for this circuit are a current-to-voltage converter, photodiode amplifier and transimpedance amplifier. An operational amplifier (op amp) 210 provides the signal gain. The op amp 210 sets the output 216 so that the current flowing through the feedback impedance $R_4$, $C_2$ 240 is equal to the current flowing through the input resistors $R_1$, $R_2$ 220, $R_3$ 230 and the photodiode detector 130. The detector generated current creates a negative voltage at the op amp output 216. The preamp DC gain (output voltage/detector current) is approximately $R_4$, and the high frequency response of the preamp is approximately $F_{cutoff} = 1/(2\pi R_4 C_2)$.

SUMMARY OF THE INVENTION

Preamp power supply rails need to provide enough headroom to allow a signal to be measured under high ambient light conditions. That is, the magnitude of the power supply voltage needs to be large enough to avoid signal saturation when the signal DC component is large. A larger supply voltage, however, results in higher preamp power consumption. A power supply rail controller advantageously reduces preamplifier power consumption by operating the preamp from a lower voltage power supply under low ambient light conditions and switching to a higher voltage power supply when necessary during high ambient light conditions.

One aspect of a power supply rail controller is a preamplifier having a signal input, a power input and a signal output. The signal input is adapted to receive a detector response to optical radiation. A first power supply generates a first voltage and a second power supply generates a second voltage, where the magnitude of the second voltage is greater than the magnitude of the first voltage. A voltage selector provides an enable output responsive to the signal output, and the power input is adapted to receive power from either the first power supply or the second power supply as determined by the enable output.

Another aspect of a power supply rail controller is a method comprising the steps of preamplifying a detector signal input utilizing a power input so as to generate a signal output, generating a low voltage for the power input so as to lower power consumption and generating a high voltage for the power input so as to reduce distortion on the signal output. Further steps include setting a threshold voltage, monitoring the signal output in relation to the threshold voltage, and selecting one of the low voltage and the high voltage for the power input in response to the monitoring step.

A further aspect of a power supply rail controller comprises a preamplifier means for inputting a detector signal and providing gain to generate an output signal. A first supply means generates a low supply voltage to the amplifier means. A second supply means generates a high supply voltage to the amplifier means. A voltage selector means enables one of said first and second supply means in response to the output signal.

Yet another aspect of a power supply rail controller operates on an analog component having a signal input, a power input and a signal output. A voltage controller provides a control output responsive to the signal output. A power supply generates a voltage for the power input, where the voltage is responsive to the control output. The voltage is reduced in magnitude to reduce power dissipation and increased in magnitude to avoid signal distortion.

DETAILED DESCRIPTION OF THE PREFERRED EMBODIMENT

Figure 3:
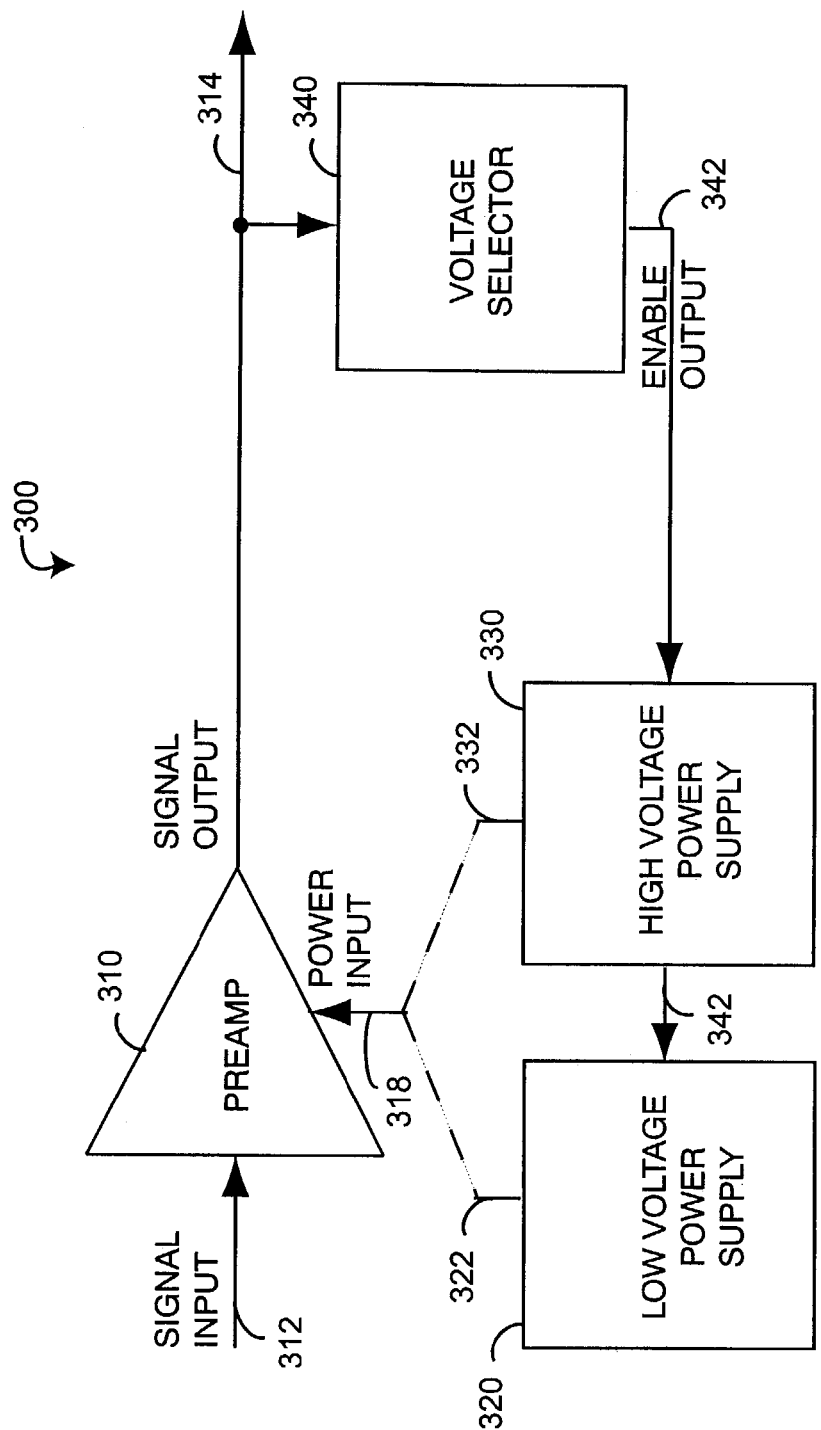
FIG. 3 is a top-level block diagram of a power supply rail controller for a preamplifier.

FIG. 3 generally illustrates a power supply rail controller 300 having an preamplifier (preamp) 310, a low voltage power supply 320, a high voltage power supply 330 and a voltage selector 340. The preamp 310 has a signal input 312, a signal output 314 and a power input 318. The controller 300 advantageously lowers the preamp 310 power consumption by operating from the low voltage power supply 320 when possible and the high voltage power supply 330 when necessary to avoid saturation of the signal output 314 as the signal amplitude approaches the power supply rail. This situation can potentially occur during high ambient light conditions, as described above. The voltage selector 340 monitors the signal output 314 and generates an enable output 342 accordingly. Specifically, the enable output 342 nominally selects the low voltage power supply 320 for low preamp power dissipation and switches to the high voltage power supply 330, raising the preamp power supply rail to prevent signal distortion. The voltage selector 340 may utilize hysteresis, time delay, filtering or other mechanisms to reduce the sensitivity of the enable output 342 to the signal output 314. The enable output 342 may select the low voltage power supply 320 or the high voltage power supply 330 for the power input 318 by selectively connecting and disconnecting the supply outputs 322, 332 to the power input 318; selectively enabling or disabling one or both power supplies 320, 330; or selectively connecting or disconnecting one or both power supplies 320, 330 from a power source.

Figure 1:
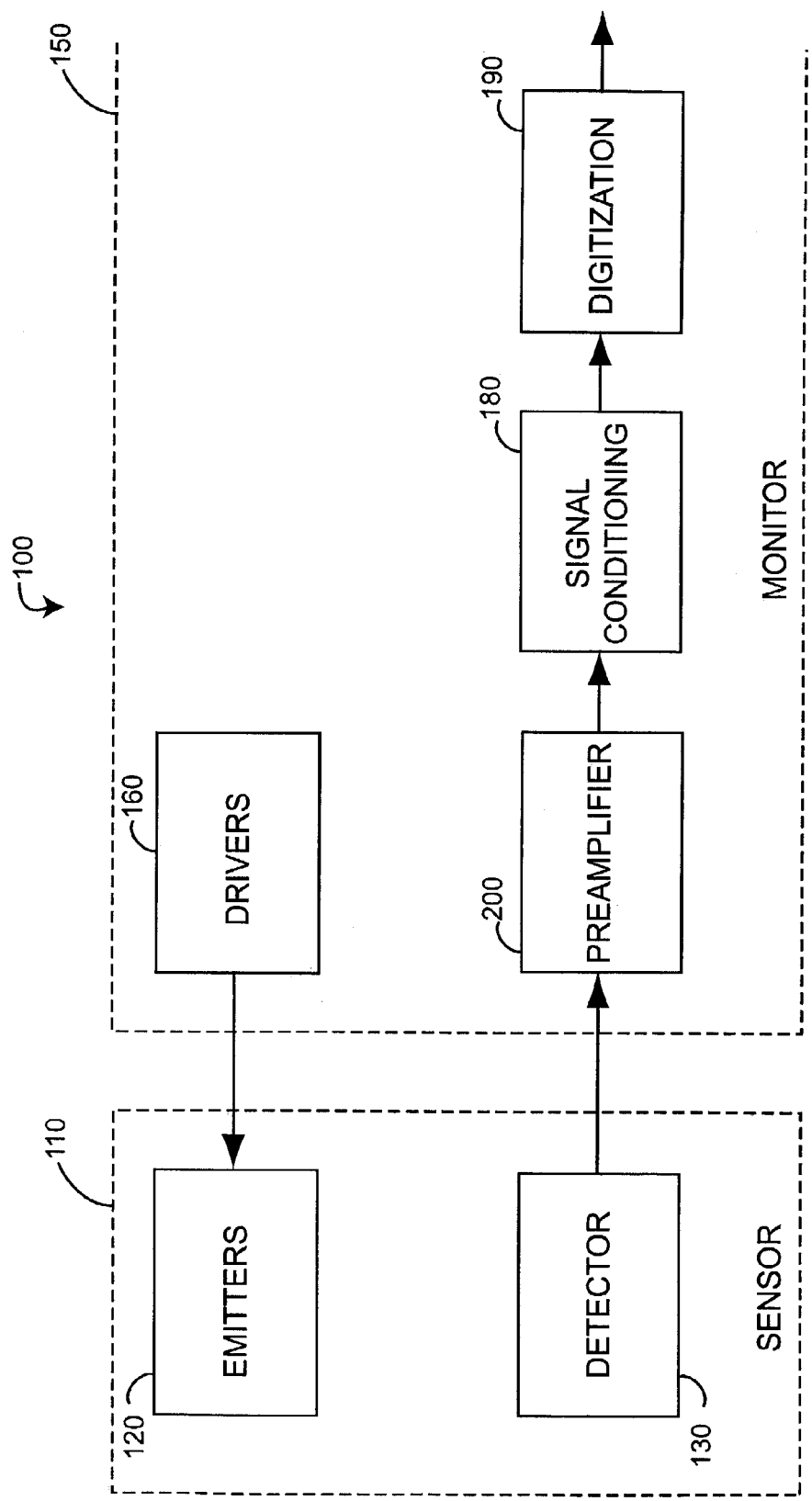
FIG. 1 is a block diagram of portions of a prior art pulse oximetry system.
Figure 4:
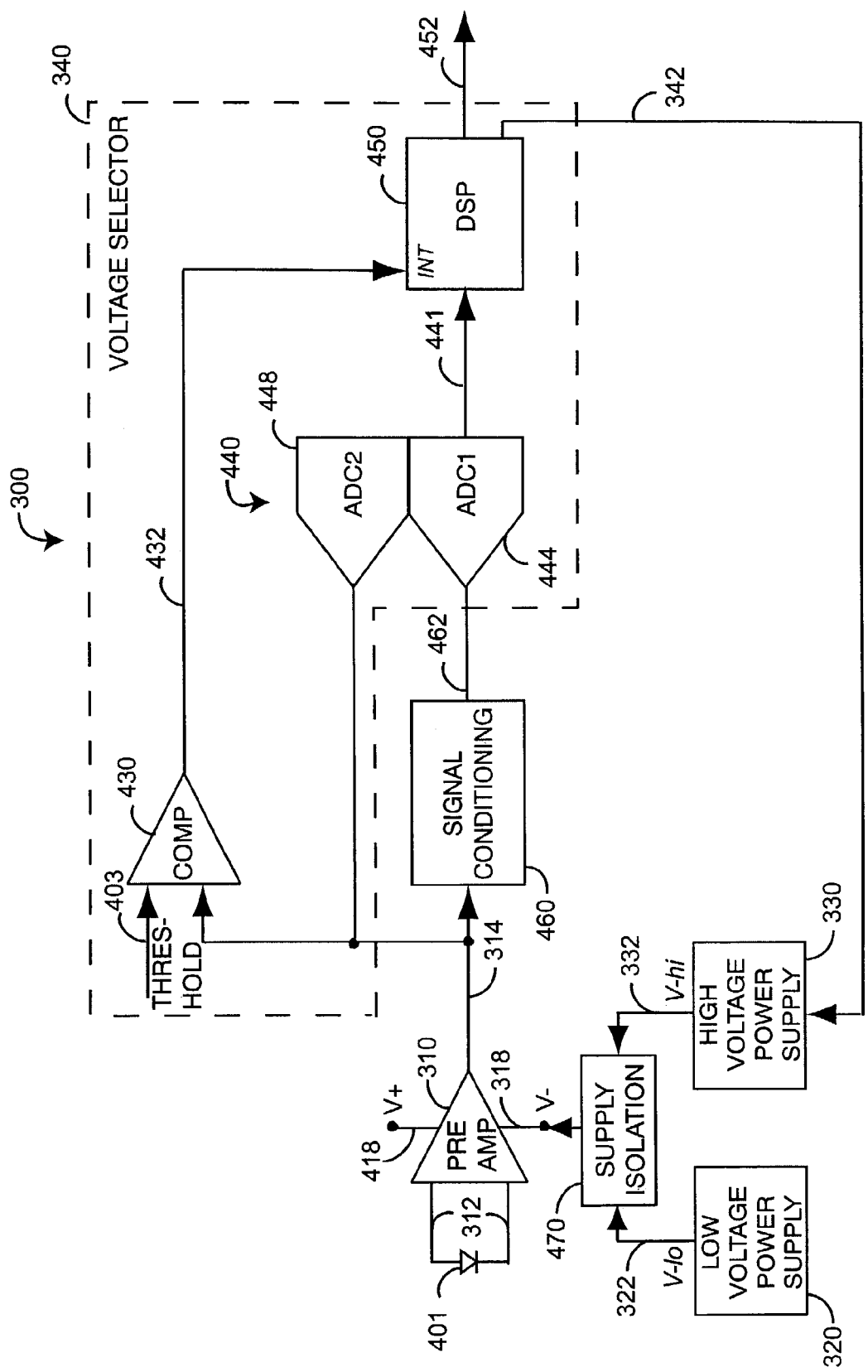
FIG. 4 is a detailed block diagram of a power supply rail controller for a preamplifier.

FIG. 4 illustrates one embodiment of a power supply rail controller 300 having a preamp 310 with a signal input 312, a signal output 314, a low voltage power supply 320, a high voltage power supply 330 and a voltage selector 340, as described with respect to FIG. 3, above. The signal input 312 is a differential input connecting to a photodiode detector 401. The preamp 310 has a negative power input 318 and a positive power input 418. The negative power input 318 is selectively powered by one of the power supplies 320, 330, as described with respect to FIG. 3, above. In particular, the low voltage power supply 320 provides a negative voltage output V-lo 322, and the high voltage power supply 330 provides a negative voltage output V-hi 332. The high voltage power supply 330 is selectively enabled by the enable output 342. The low voltage power supply 320 is always enabled. A supply isolation element 470 connects the V-lo and V-hi outputs 322, 332 to the negative power input 318 and allows the high voltage power supply 332, when enabled, to pull the negative power input 318 to a more negative voltage. The preamp 310, signal conditioning 460 and ADC 444 provide a sensor front-end for the DSP 450, such as described with respect to FIG. 1, above.

As shown in FIG. 4, the voltage selector 340 has a comparator 430, ADC 448 and a digital signal processor (DSP) 450. The DSP 450 advantageously processes a voltage selection algorithm in addition to signal processing of the detector 401 output, such as pulse oximetry spectral analysis as described with respect to FIG. 1, above. The comparator 430 compares a threshold value 403 to the amplifier output 314. The threshold 430 sets a trigger point for switching the preamp power input 318 from V-lo to V-hi. In particular, when the preamp output 314 exceeds the threshold 403, the comparator output 432 is asserted, generating an interrupt INT input to the DSP 450. The threshold 403 is set so that the DSP 450 will have time to respond to this potential signal saturation condition. Responding to the interrupt, the DSP 450 changes the state of the enable output so as to enable the high voltage power supply 330. The DSP 450 then monitors the preamp output 314 via the ADC 448. A DSP algorithm determines when to disable the high voltage power supply 330 with the power control output 342 so as to reduce power consumption. In particular, the DSP 450 determines if the amplifier output 314 is below a predetermined magnitude so as to insure that the comparator 430 is unlikely to trigger an interrupt shortly after the preamp power input 318 reverts back to the V-lo output 322.

In a particular embodiment, the ADCs 440 incorporate a dual channel device, such as a PCM3002 dual 20 bit CODEC available from Texas Instruments, which allows continuous digitization of the conditioned detector signal 462 by a first channel ADC 444 and intermittent monitoring of the amplifier output 314 as one of multiple diagnostic inputs to a second channel ADC 448. The enable output 342 is set and reset as one flag bit in a shift register providing output signals. The comparator threshold 403 is set to a predetermined value so that the DSP interrupt 432 is triggered when the preamp output 314 has exceeded about 60% of the allowable voltage range at the V-lo power supply voltage 322. Before reverting back to the low voltage power supply 322, the DSP 450 determines that the preamp output 314 will be no greater than 30% of the allowable voltage range at the V-lo power supply voltage 322. In one embodiment, the 30% threshold is monitored for a period of one minute before reverting back to the low voltage.

Figure 5:
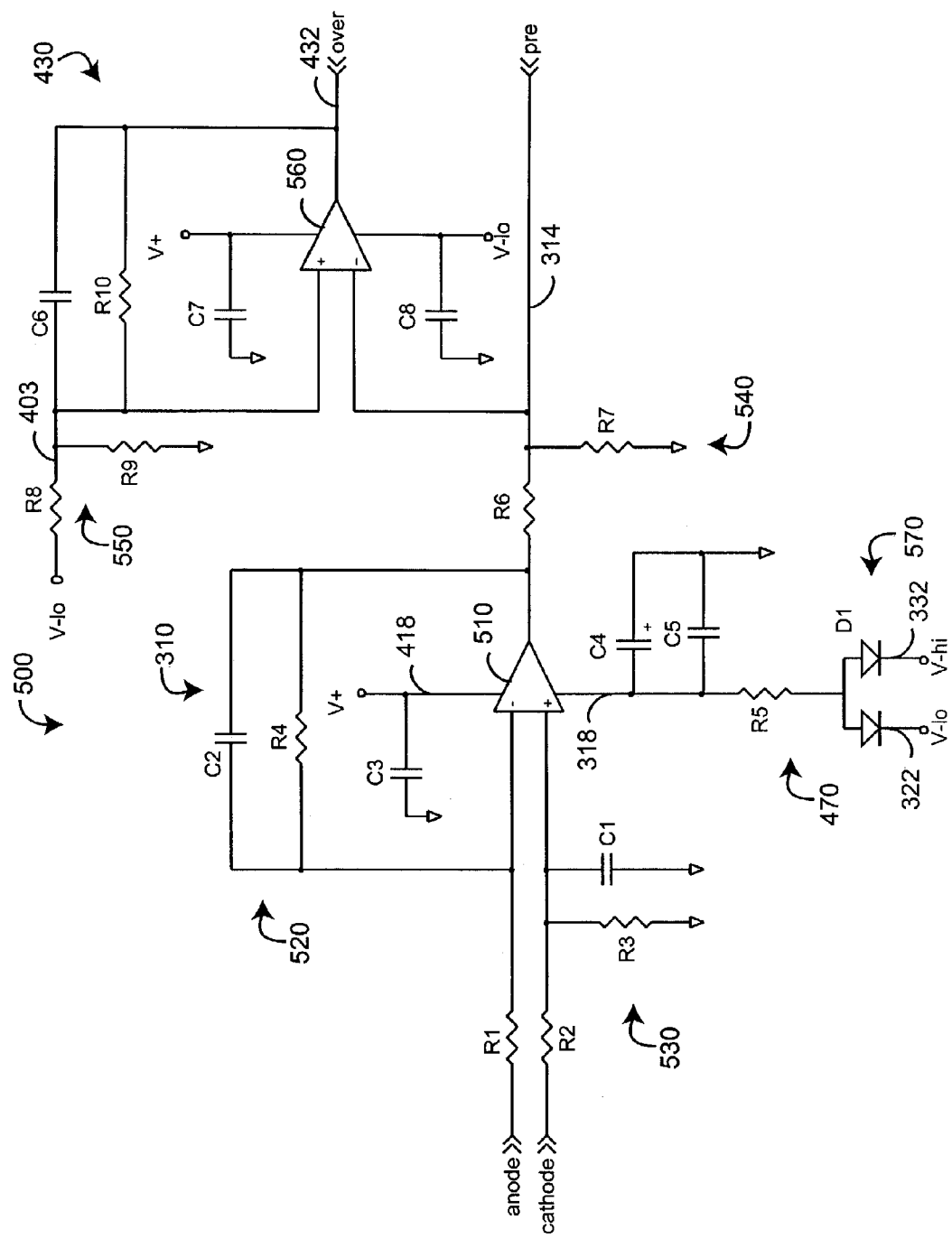
FIG. 5 is a schematic diagram of a preamplifier and comparator for a power supply rail controller embodiment.

FIG. 5 illustrates an preamp 310 and comparator 430 circuit embodiment for a power supply rail controller 300 (FIG. 4), as described with respect to FIG. 4, above. The preamp 310 is configured around an operational amplifier (op amp) 510 such as an AD820, available from Analog Device. The comparator 430 is configured around a comparator 560, such as a LMC7211, available from National Semiconductor. The op amp negative power input 318 is operated from V-lo output 322 having a nominal value of about −3VDC and a V-hi output 332 having a nominal value of about −25VDC. The V-lo output 322 is provided by a Maxim 1721 charge pump voltage supply. The V-hi output 332 is provided by a Linear Technologies LT1611 inverting switching regular. Isolation between the two outputs is achieved by a diode pair D1 570, such as an industry standard BAT54A. Because the op amp output is always negative when there is detector current, the positive supply voltage may be a low voltage to reduce power. The op amp 510 and comparator 560 positive supply voltage V+ 418 is nominally about +3VDC. The comparator 560 negative supply voltage V− is nominally about −3VDC.

As shown in FIG. 5, the threshold 403 is determined by the voltage divider $R_8$, $R_9$ 550. In a particular embodiment, $R_8$=100K and $R_9$=2.74K. Resistors $R_6$ and $R_7$ scale the preamp output 314 to fit within the range of the ADC 444 (FIG. 4). In a particular embodiment, $R_6$=100KΩ and $R_3$=5.23KΩ. Capacitors $C_3$, $C_7$, and $C_8$ are power supply bypass capacitors, such as C=1.0 μF. Resistors $R_5$ and capacitors $C_4$ and $C_5$ filter the preamp negative supply. In a particular embodiment, $R_5$=20Ω, $C_4$=3.3 μF and $C_5$=0.1 μF. The comparator hysterises is determined by $R_{10}$ and $C_6$, such as, in a particular embodiment, R=1 MΩ and C=22 pF. Resistors $R_1$ and $R_2$, in conjunction with a choke (not shown) filter EMI and ESD from the preamp input and suppress emissions from the circuit board containing these components. In a particular embodiment, $R_1$=$R_2$=1KΩ.

Figure 2:
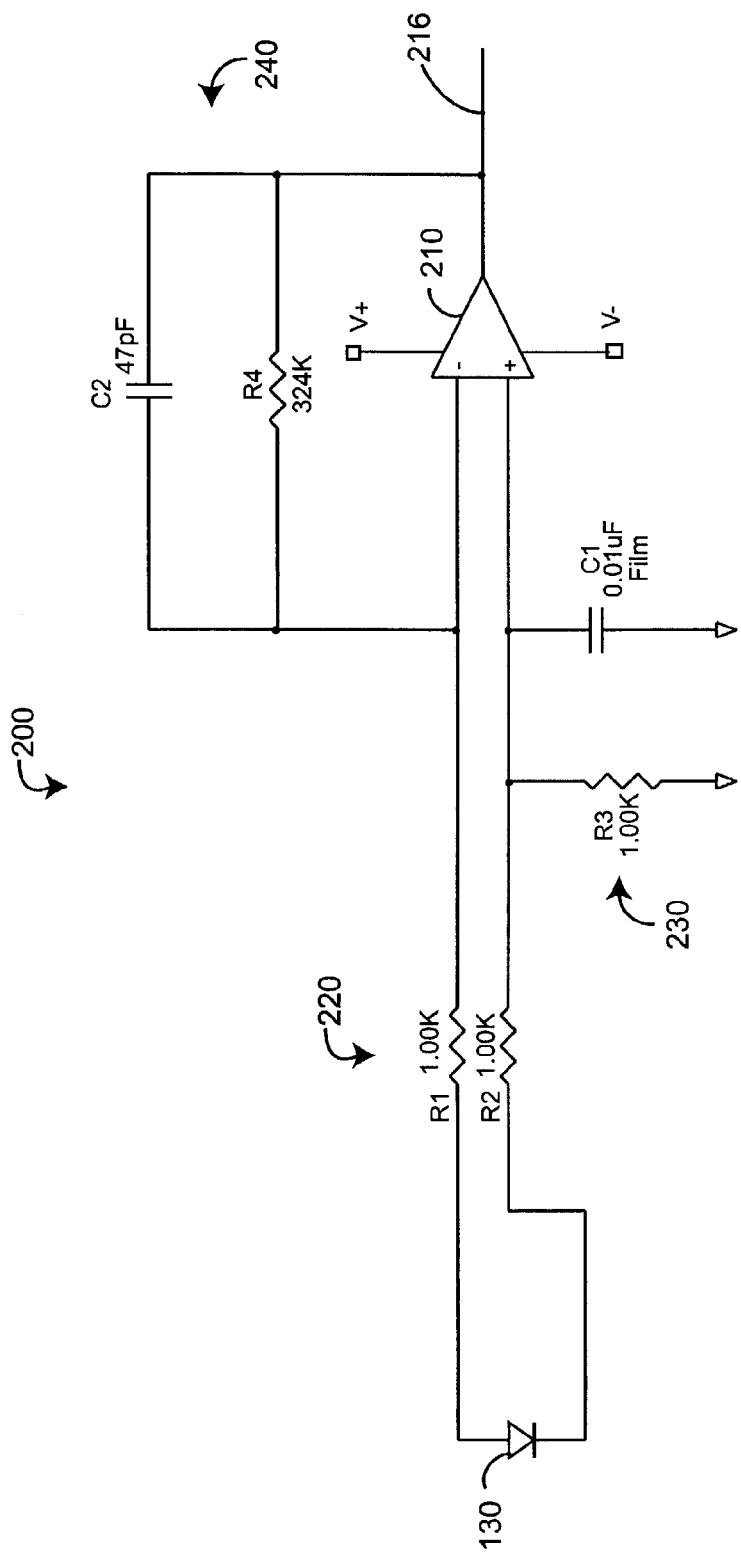
FIG. 2 is a schematic diagram of a prior art detector preamplifier.

Also shown in FIG. 5, the preamp circuit 310 is advantageously configured with differential inputs. In particular, the noninverting load resistance $R_3$ 530 matches the feedback resistance $R_4$ 520, and $C_1=C_2$, providing improved common mode noise rejection as compared with a prior art single-ended preamp such as described with respect to FIG. 2, above. The preamp DC gain (output voltage/detector current) is $R_3+R_4$, and the high frequency response is $F_{cutoff}=1/[2\pi(R_4C_2)]$. In a particular embodiment, $R_3=R_4=162K\Omega$ and $C_1=C_2=100$ pF. The resistor and capacitor values can be adjusted for different gain or bandwidth requirements, as long as the R and C values match each other. The differential input preamp achieves better common mode rejection (CMR) as compared with a single-ended preamp (FIG. 2). That is, there is higher attenuation of common-mode noise. In pulse oximetry applications, a source of common-mode noise include triboelectric noise introduced on the photodiode wires of the patient cable interconnecting the sensor and monitor. Another source of common-mode noise is 50 and 60 Hz power line noise. Another advantage of the differential input preamp includes a lower DC offset.

Figure 6:
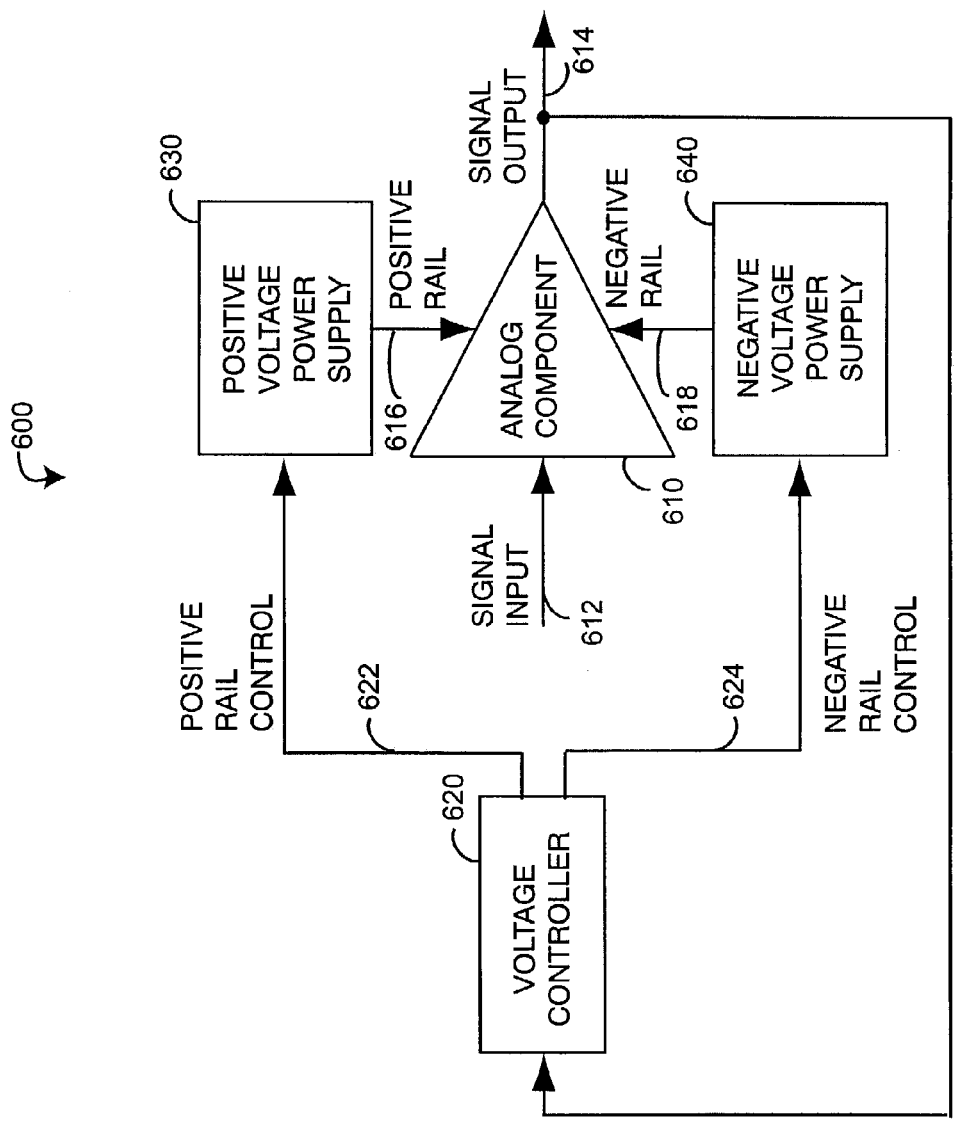
FIG. 6 is a top-level block diagram of a power supply rail controller for an active analog component.

FIG. 6 illustrates a generalized power supply rail controller 600. A power supply rail controller has been described above with respect to a preamp having a signal output with a potentially large DC component. Further, only one power supply rail was varied, and it varied between two discrete voltages. A power supply rail controller 600, however, may operate to reduce power dissipation in other active analog components 610, such as amplifiers, filters and buffers to name a few, and over other operating conditions. For example, a power supply rail controller 600 may monitor a component signal output 614 having a positive DC component, a negative DC component or no DC component. A voltage controller 620 may be a microprocessor, a DSP, or discrete analog or digital components or a combination of these. The voltage controller 620 provides a positive rail control 622 or a negative rail control 624 or both, which are responsive to the signal output 614. That is, the power supply rail controller 600 may operate on both the positive power supply rail 616 and the negative power supply rail 618, either in tandem or separately. In this manner, the voltage controller 620 increases a positive power supply voltage 630, a negative power supply voltage 640 or both to increase the rail-to-rail maximum signal when the signal magnitude is large and reduces one or both power supply voltages 630, 640 when the signal magnitude is small. In this context, signal magnitude is a combination of DC offset and signal strength. In addition, the rail voltage may be varied discretely using more than two voltages from one or more power supplies, or may be varied continuously, again from one or more power supplies.

A power supply rail controller has been disclosed in detail in connection with various embodiments. These embodiments are disclosed by way of examples only and are not to limit the scope of the claims that follow. One of ordinary skill in the art will appreciate many variations and modifications.

What is claimed is:

1. A power supply rail controller comprising:
    a preamplifier having a signal input, a power input and a signal output, said signal input adapted to receive a detector response to optical radiation;
    a first power supply generating a first voltage;
    a second power supply generating a second voltage, the magnitude of said second voltage being greater than the magnitude of said first voltage; and
    a voltage selector providing an enable output responsive to said signal output,
    wherein said power input is adapted to receive power from one of said first power supply and said second power supply as selected by said enable output.

2. The power supply rail controller according to claim 1 wherein said voltage selector comprises:
    a comparator having a first input, a second input and a trigger output,
    said first input set to a predetermined first threshold voltage,
    said second input in communications with said signal output so that said trigger output is responsive to said signal output compared to said first threshold voltage,
    said second power supply selected by said enable output in response to said trigger output.

3. The power supply rail controller according to claim 1 wherein said voltage selector comprises:
    a digital signal processor (DSP) generating said enable output;
    a voltage selection algorithm configured to execute on said DSP in response to said trigger output; and
    a second threshold voltage embedded within said selection algorithm,
    said DSP in communications with said signal output, and
    said second power supply being disabled by said enable output in response to the magnitude of said signal output being less than the magnitude of said second threshold voltage.

4. The power supply rail controller according to claim 1 further comprising:
    a supply isolation having a first input from said first power supply and a second input from said second power supply and a power output in communications with said power input,
    said first power supply being always enabled,
    said second power supply being selectively enabled, and
    said supply isolation allowing said power input to be pulled to said second voltage when said second power supply is enabled.

5. The power supply rail controller according to claim 1 wherein said preamplifier comprises:
    a first RC network providing feedback from said signal output to an inverting input; and
    a second RC network providing a load to a non-inverting input,
    said first RC network identical to said second RC network so that said signal input is a balanced, differential input.

6. A power supply rail controller method comprising the steps of:
    preamplifying a detector signal input utilizing a power input so as to generate a signal output;
    generating a low voltage for said power input so as to lower power consumption;
    generating a high voltage for said power input so as to reduce distortion on said signal output;
    setting a threshold voltage;
    monitoring said signal output in relation to said threshold voltage; and
    selecting one of said low voltage and said high voltage for said power input in response to said monitoring step.

7. The power supply rail controller method according to claim 6 wherein said preamplifying step comprises the substep of providing a balanced input to said detector input signal configured to amplify differential voltage and reject common mode voltage.

8. The power supply rail controller method according to claim 6 wherein said setting step comprises the substeps of:

calculating a maximum signal output before saturation with said low voltage on said power input; and predetermining a percentage of said maximum signal output as said threshold voltage.

9. The power supply rail controller method according to claim 8 wherein said predetermining step comprises the substeps of:

calculating a first percentage for a first threshold voltage to use when selecting said high voltage so as to allow sufficient time to avoid signal distortion; and calculating a second percentage for a second threshold voltage to use when selecting said low voltage, said second percentage sufficiently less than said first percentage so as to reduce sensitivity to said signal output.

10. The power supply rail controller method according to claim 6 wherein said monitoring step comprises the substeps of:

comparing said signal output to said threshold voltage; and triggering a processor interrupt when said signal output exceeds said threshold voltage.

11. The power supply rail controller method according to claim 10 wherein said monitoring step comprises the further substep of indicating when said signal output returns below a lower second threshold voltage.

12. The power supply rail controller method according to claim 10 wherein said selecting step comprises the substep of selecting said high voltage in response to said triggering substep.

13. The power supply rail controller method according to claim 11 wherein said selecting step comprises the substep of selecting said low voltage in response to said indicating substep.

14. The power supply rail controller method according to claim 6 wherein said selecting step comprises the substeps of:

enabling said low voltage for said power input;

isolating said low voltage from said high voltage; and selectively enabling said high voltage for said power input so as to pull said power input from said low voltage to said high voltage.

15. A power supply rail controller comprising:

a preamplifier means for inputting a detector signal and providing gain to generate an output signal;

a first supply means for generating a low supply voltage to said preamplifier means;

a second supply means for generating a high supply voltage to said preamplifier means; and a voltage selection means for enabling one of said first and second supply means in response to said output signal.

16. The power supply rail controller according to claim 15 further comprising a isolation means for routing said low supply voltage and said high supply voltage to said preamplifier means.

17. The power supply rail controller according to claim 15 wherein said voltage selection means comprises a comparator means for indicating when said output signal exceeds a predetermined threshold so as to enable said second supply means.

18. The power supply rail controller according to claim 15 wherein said voltage selection means comprises a processor means for monitoring said output signal and deciding when to re-enable said first supply means.

19. The power supply rail controller according to claim 15 wherein said preamplifier means comprises a differential input means for rejecting common mode noise.

20. A power supply rail controller comprising:

an analog component having a signal input, a power input and a signal output;

a voltage controller providing a control output responsive to said signal output; and a power supply generating a voltage for said power input, wherein said voltage is responsive to said control output so that said voltage is reduced in magnitude to reduce power dissipation and increased in magnitude to avoid signal distortion.

* * * * *